United States Patent [19]

Kesling et al.

[11] 4,350,487
[45] Sep. 21, 1982

[54] LOCK PIN

[75] Inventors: Peter C. Kesling, LaPorte; Dennis B. Henderlong, Michigan City, both of Ind.

[73] Assignee: TP Laboratories, Inc., LaPorte, Ind.

[21] Appl. No.: 243,832

[22] Filed: Mar. 16, 1981

Related U.S. Application Data

[63] Continuation-in-part of Ser. No. 139,869, Apr. 14, 1980, abandoned.

[51] Int. Cl.³ .............................................. A61C 3/00
[52] U.S. Cl. ........................................ 433/14; 433/21
[58] Field of Search ............................. 433/14, 15, 21

[56] References Cited

U.S. PATENT DOCUMENTS

| | | | |
|---|---|---|---|
| 2,930,126 | 3/1960 | Kesling | 433/14 |
| 3,134,171 | 5/1964 | Kessler | 433/14 |
| 3,408,739 | 11/1968 | Johnson | 433/14 |
| 3,445,933 | 5/1969 | Kesling | 433/14 |
| 3,574,940 | 4/1971 | Allesee | 433/14 |
| 3,686,758 | 8/1972 | Kesling | 433/14 |
| 3,793,730 | 2/1974 | Begg et al. | 433/14 |
| 3,835,539 | 9/1974 | Wallsheim | 433/14 |
| 4,180,912 | 1/1980 | Kesling | 433/14 |
| 4,242,085 | 12/1980 | Wallsheim | 433/14 |

OTHER PUBLICATIONS

TP Lab. Inc., catalog 905, 1978, p. 49 (lingual lock pin).

Primary Examiner—Paul J. Hirsch
Assistant Examiner—John J. Wilson
Attorney, Agent, or Firm—Lloyd L. Zickert

[57] ABSTRACT

Lock pin for a bracket having a body with an occlusogingivally extending opening, attaching flanges on the lingual side of the body for attaching the bracket to a tooth, and an archwire slot at the gingivolingual corner of the body for receiving one or more archwires, wherein the lock pin includes a tail or shank extending lingual of an archwire or archwires in the archwire slot and with a part having a mesiodistal width that fits snugly between the attaching flanges to prevent relative rotation between the pin and the bracket and a head fitting in the archwire slot having an archwire engaging face of a length at least equal to half the mesiodistal width of the bracket such that a part of the head extends beyond one side of the bracket body so that precise mesiodistal control between the bracket and the archwire can be achieved. In an alternate form the tail is disposed buccal to the head and the archwire.

25 Claims, 17 Drawing Figures

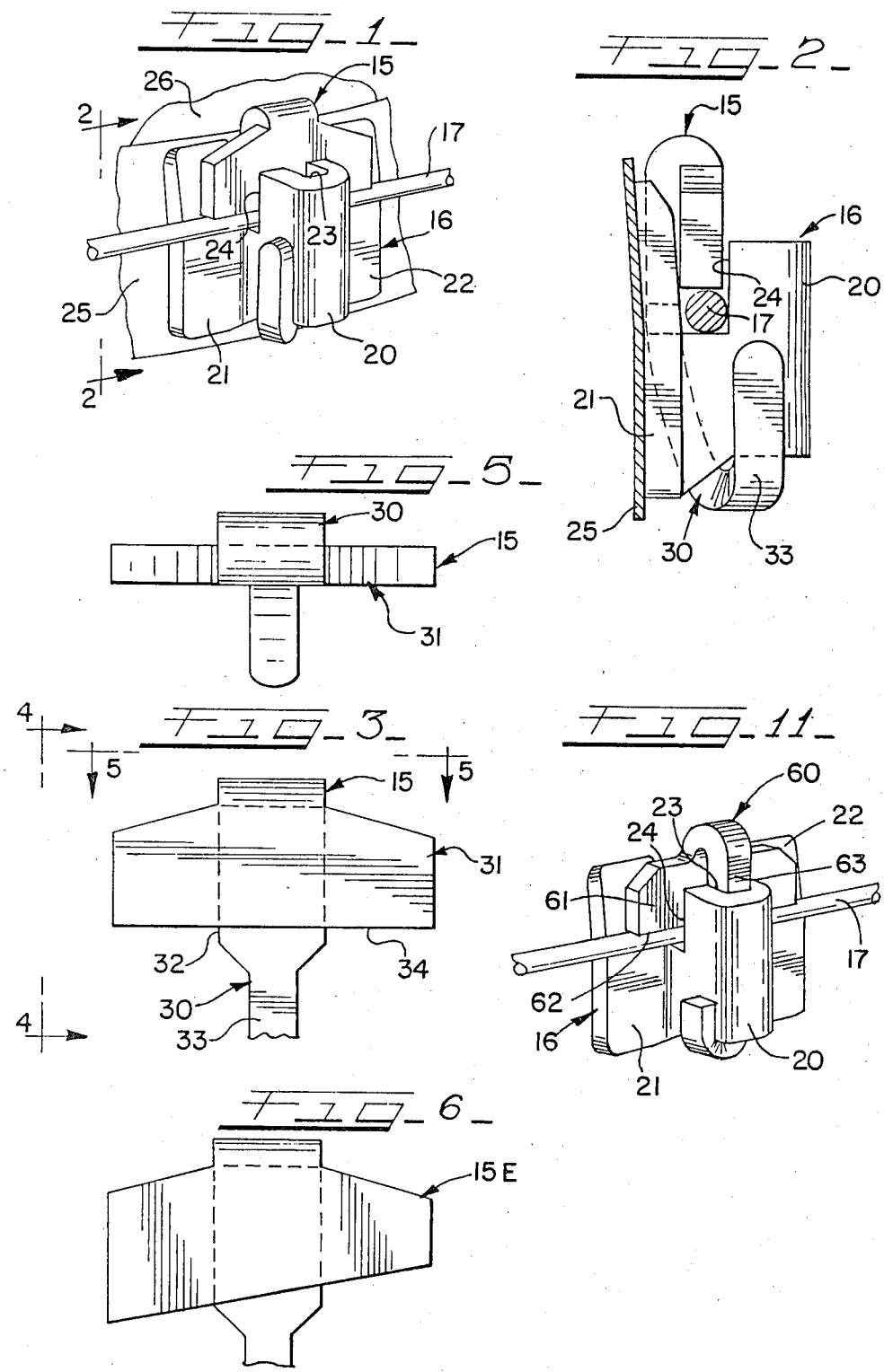

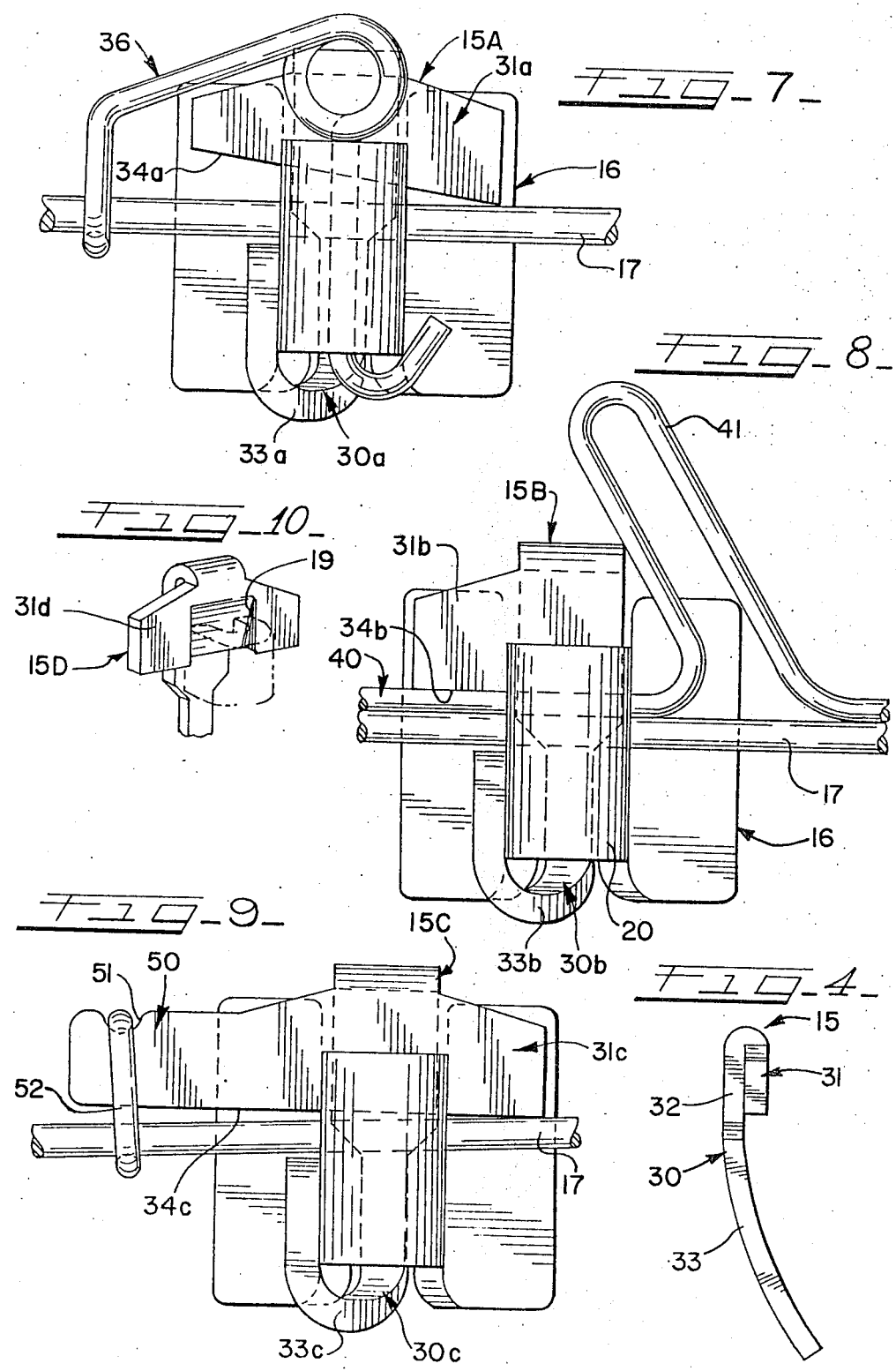

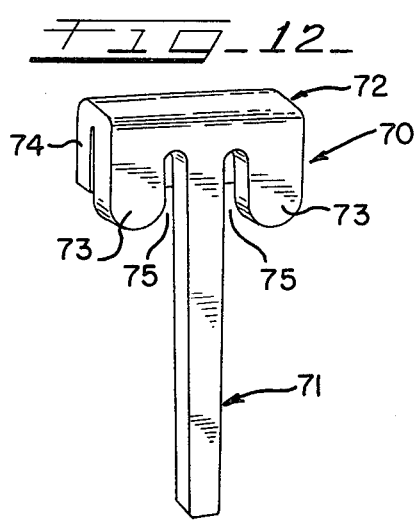
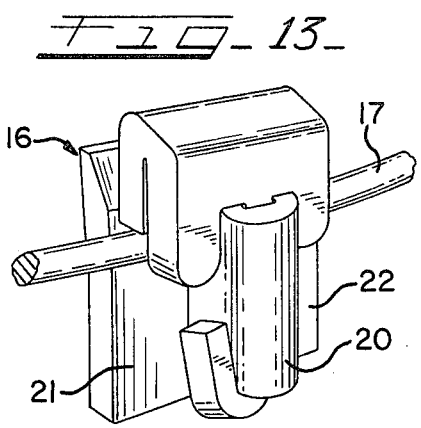
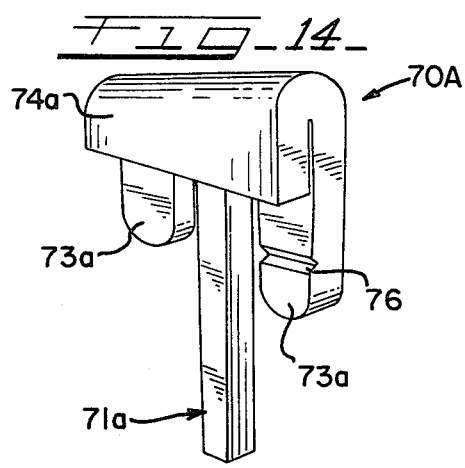
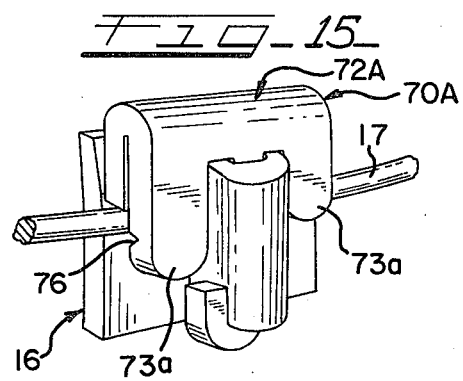
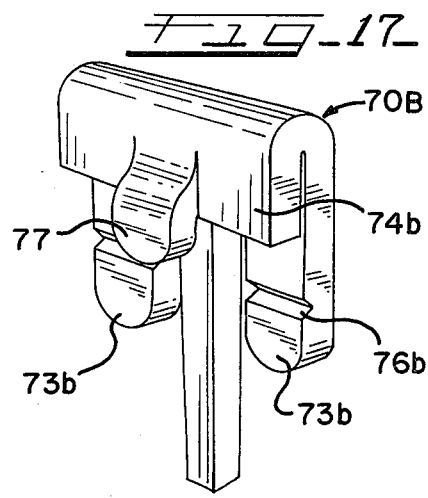
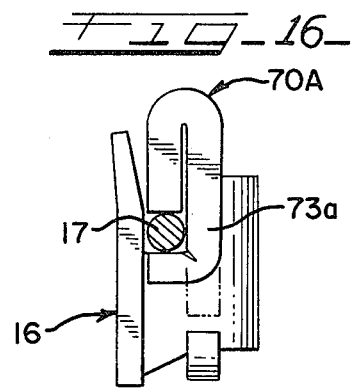

LOCK PIN

This application is a continuation-in-part application of our application Ser. No. 139,869, filed Apr. 14, 1980, now abandoned.

This invention relates in general to a lock pin, and more particularly to a lock pin for use in combination with a light wire bracket having an occlusogingivally extending opening and an archwire slot where the lock pin coacts with the bracket to engage the archwire and control mesiodistal inclination between the tooth on which the bracket is mounted and the archwire.

While the lock pin of the present invention is particularly useful for locking or connecting an archwire or archwires to light wire brackets used in the Begg technique and particularly a bracket like that made by TP Laboratories, Inc. of LaPorte, Ind. and called a TP 256-500 bracket, it should be appreciated that the lock pin could be used with other types of light wire brackets. More particularly, the lock pin would be usable with a bracket having a body with an occlusogingivally extending opening, attaching flanges at the lingual side of the body and an archwire slot at the gingivolingual corner of the body.

Heretofore, in order to control mesiodistal inclination of a tooth in any stage of treatment, de-activated uprighting springs were normally employed. Use of uprighting springs during any stage, as compared to use of a lock pin, results in an inferior oral hygiene situation, as food particles can more easily become entrapped by the spring. Thus, use of lock pins promotes better oral hygiene. Moreover, when it is desired to use uprighting springs as a means to control mesiodistal inclination, it is necessary to adjust the springs to a de-activated state which requires time of the orthodontist and is often difficult to accurately achieve.

It has been heretofore known to provide various types of lock pins for coacting with brackets including light wire brackets for the purpose of locking one or more archwires to a bracket. However, it has not been known to heretofore provide a lock pin having sufficient strength such that it is capable of controlling mesiodistal inclination between a bracket and the archwire.

The present invention overcomes difficulties heretofore encountered in controlling mesiodistal inclination by providing a lock pin having the required strength such that it is capable of coacting with a light wire bracket for controlling mesiodistal inclination and avoiding the problems heretofore encountered by the use of uprighting springs for obtaining such control. It is therefore appreciated that the lock pin of the present invention will replace the use of mesiodistal uprighting springs in order to hold individual teeth at desired inclinations, thereby preventing "bounce-back" of roots. Use of the lock pin of the present invention promotes better oral hygiene than use of an uprighting spring. Moreover, the lock pin of the present invention may also be used to limit free tipping of a tooth during a stage of treatment as is sometimes required in connection with orthodontically treating lower canines.

The lock pin of the present invention in one embodiment includes a tail that is positioned lingual of the archwire or archwires and having a part that is of such a mesiodistal width to fit snugly between the attaching flanges in the area of the archwire slot to prevent relative rotational movement between the pin and the bracket along a buccolingual axis. A head is provided on the end of the tail where the tail fits between the attaching flanges and defines an elongated archwire engaging face that is at least one-half the mesiodistal width of the entire bracket structure such that at least a part thereof extends beyond one side of the bracket body. Additionally, the head may be of such a length as to extend beyond both sides of the body to provide an archwire engaging face extending through the archwire slot of the bracket and beyond the opposite sides of the body. In that event, the head may be indented to receive the body and provide additional stability between the head and the bracket. In an alternate form, the tail may be positioned on the buccal side of the head. Moreover, the head may be oriented perpendicular to the tail or at an angle less than or more than ninety degrees relative to the tail, so that the archwire engaging face extends ninety degrees to the vertical axis of the bracket or angled ten degrees left or right. A further modified version would include providing an extension on one end of the head which would extend beyond the mesial or distal side of the bracket so that it can function to receive an elastomeric ring or a steel or elastic ligature for drawing the head and archwire toward each other for added control and/or movement purposes. Additionally, the head may have ears extending along the tail to engage the body of the bracket and provide additional stability and control. One of the ears could be long enough to be bent over the archwire and provide further increased control.

It is therefore an object of the present invention to provide a new and improved lock pin for a light wire bracket having the required strength such that it is capable of controlling mesiodistal inclination between the bracket and the archwire or archwires locked to the bracket by the lock pin.

A further object of the present invention is to provide a lock pin capable of controlling mesiodistal inclination between the bracket and the archwire to thereby take the place of heretofore used de-activated uprighting springs and accordingly promote better oral hygiene.

Other objects, features and advantages of the invention will be apparent from the following detailed disclosure, taken in conjunction with the accompanying sheets of drawings, wherein like reference numerals refer to like parts, in which:

FIG. 1 is a perspective view of a bracket mounted on a tooth having an archwire in its slot and a lock pin mounted therein according to the invention;

FIG. 2 is a side elevational view of the lock pin and bracket assembly of FIG. 1 and looking in the direction of the arrows of line 2—2;

FIG. 3 is a fragmentary front elevational view of a lock pin according to the invention prior to its being mounted on a bracket;

FIG. 4 is a side elevational view of the pin of FIG. 3 and looking along line 4—4 of FIG. 3;

FIG. 5 is a top plan view of the pin of FIG. 3 and looking along line 5—5 in FIG. 3;

FIG. 6 is a view similar to FIG. 3 but showing a modified head where the archwire engaging surface is inclined to the pin tail;

FIG. 7 is a modification of the lock pin of the present invention and of opposite hand to the pin of FIG. 6 illustrating the head to be angularly related to the tail at an angle other than ninety degrees;

FIG. 8 is a front elevational view of a bracket archwire and lock pin assembly and illustrating a modified lock pin where the head extends only in one direction from the body;

FIG. 9 is a front elevational view of a lock pin and bracket assembly wherein the lock pin is a modified version with an extension at one end of the head for purposes of enabling the head and archwire to be drawn together with a ligature;

FIG. 10 is a fragmentary perspective view of a modification where the head is indented to engagably receive a part of the bracket body;

FIG. 11 is a perspective view like FIG. 1 but illustrating a modified pin where the tail is buccal to the head;

FIG. 12 is a perspective view of a modified lock pin according to the invention;

FIG. 13 is a perspective view of the lock pin of FIG. 12 mounted on a bracket and shown in connection with the retaining of an archwire on the bracket;

FIG. 14 is a rear perspective view of a further modified lock pin according to the invention which differs from the embodiment of FIG. 12 in that the ears engaging the bracket body are longer so that at least one of the ears can be bent over the archwire if desired;

FIG. 15 is a perspective view of a lock pin like that of FIG. 14 mounted on a bracket having an archwire in the archwire slot and where the ears are not bent over the wire;

FIG. 16 is a side elevational view of the bracket and pin shown in FIG. 15 and having one of the ears bent over the wire to increase the control between the appliance and the wire; and FIG. 17 is a rear perspective view of a still further modified lock pin according to the invention having an offset lingual portion extending from the head to fit lingually of the archwire and between the welding flanges of the bracket to provide further stability.

Referring now to the drawings, and particularly to FIGS. 1 to 5, a lock pin embodiment of the invention is illustrated and shown in FIGS. 1 and 2 as being mounted on a bracket and in working relationship with the bracket and an archwire and in FIGS. 3 to 5 prior to being mounted on a bracket. The lock pin illustrated in FIGS. 1 to 5 is generally designated by the numeral 15 and as shown in FIGS. 1 and 2 is mounted on a light wire bracket generally indicated by the numeral 16 for attaching an archwire 17 to the bracket.

The bracket 16 includes a body 20 having at the lingual side thereof spaced apart attaching flanges 21 and 22. The body 20 is provided with an occlusogingivally extending opening 23 and a mesiodistally extending archwire slot 24 at the gingivolingual corner of the body. It will be understood that the opening 23 extends lingually between the attaching flanges and that the attaching flanges, often defined as welding flanges, may be secured by welding or the like to a band 25 that is in turn cemented to a tooth. Alternatively, the attaching flanges may be suitably attached by welding or soldering to a mesh base that would in turn be direct bonded to a tooth by an adhesive. In either case the bracket is attached to the tooth. The archwire slot 24 is in reality defined by a notch formed in the body and the adjacent attaching flanges 21 and 22 and which has a buccolingual depth slightly greater than the maximum diameter of the archwire desired to be used with the bracket so that the archwire may be freely inserted in the slot.

The lock pin 15 includes a tail or shank 30 and a head 31. The tail 30 includes an upper part 32 having a mesiodistal width substantially the same as the mesiodistal opening between the attaching flanges such that when the lock pin is inserted into the bracket this part 32 will fit snugly between the attaching flanges and prevent relative rotation between the lock pin and the bracket along a buccolingual axis. The tail also includes a lower part 33 having a mesiodistal width substantially less than the upper part 32 and which lower part will, when inserted into the opening 23 of the bracket, be easily bendable over the occlusal end of the bracket as illustrated in FIGS. 1 and 2 in order to secure the lock pin to the bracket, as seen particularly in FIG. 4. The tail 30 has a curvature labiolingually along its length which facilitates the insertion of the pin into the bracket and bending of the tail after insertion.

The head 31 of the lock pin 30 is integral with the tail and overlaps or overlies the upper portion 32 of the tail, as best seen in FIGS. 2, 4 and 5. It can be appreciated that during the manufacture of the lock pin the head is bent back over the upper end of the tail. Heretofore, it was not known how sufficient strength could be provided in a lock pin of the type herein disclosed, and it has been found that by bending the head over the tail as in the present invention a sufficient amount of strength is obtained in order to provide a pin of such integrity that it will withstand the forces to which it may be subjected in giving mesiodistal control action.

The head 31 has a buccolingual depth substantially equal to the diameter of the archwire 17 so that it substantially fills the buccolingual depth of the archwire slot 24. The lock pin head has a mesiodistal width substantially equal to the mesiodistal width of the bracket such that the head will extend through the archwire slot and beyond the opposite sides of the body 20. It thereby defines an elongated archwire engaging face 34 that is rectilinear or straight and extends in this embodiment perpendicular to the long axis of the tail 30, as shown in FIG. 3. The face 34 engages the archwire 17 along a mesiodistal length of the archwire substantially equal to the mesiodistal width of the bracket and along a mesiodistal length greater than the archwire area engaging in the archwire slot. When the pin is properly mounted on the bracket, the free end of the tail is bent over the end of the bracket opposite the head to secure the pin in place as shown. Accordingly, the face 34 of the lock pin embodiment of FIGS. 1 to 5, as mounted on the bracket illustrated, parallels and engages the archwire, thereby controlling mesiodistal inclination between the archwire and the bracket, which results in holding individual teeth at desired inclinations and preventing "bounce-back" of tooth roots. Likewise, the pins of FIGS. 6 and 7 may, by virtue of the brackets in which they are used being so oriented to the teeth on which they are mounted, be oriented such that the wire engaging faces parallel and engage the wire.

As shown in FIG. 10, additional stability can be imparted to the lock pin by structuring the head to coact with the body of the bracket. This form generally designated as 15D has an indentation 19 formed in the head 31*d* which telescopically receives the lingual portions of the bracket body at the archwire slot 24 when the pin is in properly mounted position. Thus, the coaction between the indentation 19 of the head and the bracket body, in addition to the coaction of the upper part of the pin tail and the attaching flanges of the body, collectively serve to prevent relative rotation between the lock pin and the bracket along a buccolingual axis. The indentation 19 may be formed in any suitable manner and may even be cut straight through the head as a notch if desired.

By slightly modifying the lock pin of the present invention to change the angular relationship between the head and the tail, the pin may also be used in conjunction with an uprighting spring to limit tipping as illustrated in the assembly of FIG. 7 where the lock pin is generally designated by the numeral 15A and is shown mounted on the bracket 16 having an archwire 17 in its slot and where an uprighting spring 36 is also mounted on the bracket to effect tipping of the tooth in a clockwise direction, as illustrated by looking at the buccal side of the bracket. It should be appreciated the pin of FIGS. 1 to 5, where the tail extends at right angles to the head, may also be used in this type of assembly where the bracket may be angularly positioned on a tooth. In this embodiment, the archwire engaging face 34a of the lock pin 15A is angled relative to the tail 30a approximately ten degrees to the right. It can be readily appreciated that the tail of the uprighting spring 36 fits into the occlusogingivally extending opening of the bracket buccal of the archwire with its free end bent over the occlusal end of the bracket and the spring arm hooked over the archwire 17. Only one end of the archwire engaging face 34a engages the archwire 17. Although it will be appreciated that the entire face will engage the archwire 17 when the uprighting spring 36 has effected the tipping of the tooth so that the archwire 17 parallels and engages the archwire engaging face 34a, it should be recognized that during treatment of a patient to accomplish this function, it may be necessary to cinch up the tail of the lock pin to eliminate vertical play between the archwire and the archwire engaging face of the pin head after tipping has been accomplished. It should be further appreciated that the head 31a may be angulated relative to the tail of the pin about ten degrees to the left or opposite that shown in FIG. 7, such as illustrated by the pin 15E in FIG. 6, or to any other desired angular relationship with respect to the tail.

Another embodiment of the lock pin according to the invention is illustrated in FIG. 8 wherein the head of the lock pin differs from the heads of lock pins 15 and 15A so that an obstruction or obstacle can be avoided. In addition to mounting the archwire 17 onto the bracket 16, an auxiliary archwire 40 is also inserted into the archwire slot of the bracket and includes a torqueing spur 41 that is desired to be positioned directly adjacent to the bracket 16. The lock pin illustrated here and generally designated by the numeral 15B differs from the lock pin 15 above described in that the mesiodistal width of the head 31b has been shortened so that it extends through the archwire slot and only to one side of the bracket body 20, while still providing an elongated archwire engaging face 34b that is capable of providing mesiodistal control between the archwire and the bracket. It may be appreciated that the head 31b, while shown to be extended to the left of the bracket body as looking at the front of the bracket in FIG. 8, could extend just to the right of the bracket body if the torqueing spur were on the opposite side of the bracket.

A modified form of lock pin according to the invention is illustrated in FIG. 9 in assembly with a bracket and an archwire and differs from the lock pin 15 shown in FIGS. 1 to 5 only in that an extension is provided at one of the mesial or distal ends of the head for purposes of facilitating a connection between the head and the archwire with a suitable ligature and to thereby apply a force on the bracket toward the archwire. This lock pin is generally designated by the numeral 15C and includes a tail 30c having the head 31c at one end thereof. An extension 50 provided at one side of the head extends beyond the bracket. A notch 51 defined in the upper edge of the extension while the lower edge thereof is contiguous with the archwire engaging face 34c prevents a ligature such as that indicated at 52 from slipping along the extension while the ligature also encloses the archwire 17. Thus, the ligature connects the archwire and pin at the extension. This ligature may be in the form of an elastomeric ring or elastomeric thread which thereby applies a pulling force between the head of the pin and therefore the bracket and the archwire, since the pin is mounted to the bracket in such a way as to prevent relative rotational movement along a buccolingual axis between the pin and bracket. The opposite end of the archwire engaging face which appears as the right-hand end in FIG. 9 pushes down on the archwire. Accordingly, a rotational force is applied between the bracket and the archwire to cause rotation of the tooth until the entire archwire engaging face 34c is in engagement with the archwire 17.

It will be appreciated that the extension could be provided at either end of the head to provide the desired rotational movement. Further, it should be recognized that the length of the extension may be defined so that a suitable lever arm force can be applied to the bracket. Thus, this embodiment is useful for providing a tipping force to a tooth in the same manner as the embodiment of FIG. 7 where an uprighting spring is employed.

A further embodiment of the invention is illustrated in FIG. 11, which may be generally considered to be a reverse structure of the lock pin shown in the embodiments of FIGS. 1 to 10 in that the head for this lock pin is positioned at the lingual side of the tail and the tail is formed to coact with the opening 23 in the bracket body, thereby placing the tail at the labial or buccal side of the archwire. This lock pin is generally designated by the numeral 60 and includes a head 61 of substantially the same shape as the head in the embodiment of FIGS. 1 to 5 with an archwire engaging face or surface 62 that coacts with the archwire. In this embodiment the face is positioned at right angles to the pin tail although it could be inclined relative to the pin tail as illustrated in the embodiments of FIGS. 6 and 7. The pin also includes a tail 63 that is rectangular in cross section and dimensioned to fit into the occlusogingival opening 23 of the bracket body 20 so that any relative rotation between the pin and the bracket on the boccolingual axis is inhibited. It will be understood that the depth of the head 61 is such as to fit in the archwire slot 24 and prevent escape of the archwire 17 from the slot. The pin 60 as illustrated is in mounted relationship to the bracket wherein the end of the pin tail is bent over the bracket body as illustrated, thereby securing the pin in place. This pin embodiment would function in the same manner as the other pin embodiments, that is, to control mesiodistal inclination between the tooth on which the bracket is mounted and the archwire.

A further embodiment of the invention is illustrated in FIGS. 12 and 13 wherein the lock pin is generally designated by the numeral 70 and includes a tail or stem 71 and a head 72. The tail 71 is straight and is positioned labially of the archwire. The structure of the head differs from the embodiment of FIG. 11 essentially in that ears or tabs 73 are provided at the labial side of the head and along opposite sides of the tail 71. Further, these ears are in generally abutting relation to the archwire engaging portion 74 and overlie the archwire to provide rotational control over the tooth. The extended ears 73 define with the tail 71 slots 75 which, when the pin is mounted on the bracket as shown in FIG. 13, receive the opposed side walls of the bracket body 20 in snug enough relation in order to provide additional stability between the pin and the bracket. While two ears are shown, it could be appreciated only one may be needed for some situations.

A still further lock pin embodiment of the invention is shown in FIGS. 14 to 16 and generally designated by the numeral 70A. This embodiment differs from that in FIGS. 12 and 13 in that at least one of the ears 73a is extended or longer to come down beyond the archwire such that a part of the ear can be bent over the archwire as shown in FIG. 16 for purposes of further increasing the control between the bracket and pin combination and the archwire. In order to facilitate the bending of the ear, the lingual surface of the ear is scored at 76 as shown in FIG. 14. This embodiment also illustrates the wire engaging face to be inclined rather than perpendicular to the tail.

Another modified lock pin according to the invention is illustrated in FIG. 17 and designated generally by the numeral 70B. This lock pin differs from that shown in FIGS. 14 to 16 in that both ears 73b are the same length and scored at the lingual surface, and further in that it also includes a lug 77 extending downwardly from the archwire engaging portion 74b and offset lingually so that it will be positioned lingual of the archwire and between the attaching flanges 21 and 22, whereby further increased stability and control is established between the tooth on which the bracket is mounted on the archwire. The lug also serves to more securely retain the archwire or archwires in the slot and prevent their escape during patient treatment. It will be appreciated that such a control lug could also be incorporated with the embodiments of FIGS. 1 and 12 if desired. Moreover, the lug coacts with the tail such that it could snugly receive a rectangular archwire.

It should also be appreciated that the archwire engaging face of the archwire engaging portion of the embodiments of FIGS. 12, 14 or 17 may extend ninety degrees to the vertical axis of the bracket or it may be angled approximately ten degrees left or right to provide the desired angular position between the archwire and the bracket.

In all of the embodiments of the invention illustrated, the head is bent back over the tail or stem in order to provide sufficient strength to the lock pin so that the pin maintains its integrity during use in the mouth to provide the desired mesiodistal control. However, where strength could be otherwise provided or not needed, the head may not need to be doubled over. Indeed, one or more ears add strength to the pin to enhance the working relation between the pin and the bracket.

It will be understood that modifications and variations may be effected without departing from the scope of the novel concepts of the present invention, but it is understood that this application is to be limited only by the scope of the appended claims.

The invention is hereby claimed as follows:

1. In combination with a bracket having a body with an occlusogingivally extending opening, attaching flanges at the lingual side of the body, and a mesiodistally extending archwire slot at the gingivolingual corner of said body, a lock pin for locking one or more archwires against the bottom of said slot comprising a tail extending into said opening, means coplanar with the tail and coacting with the bracket to prevent relative rotational movement between the bracket and the pin along a buccolingual axis, and a head on the end of the pin received in said slot in overlying relationship to said archwire or archwires and in overlapping abutting relationship to said means and having a mesiodistal width at least equal to about one-half the mesiodistal width of the bracket to extend beyond at least one side of the body and a buccolingual depth substantially equal to that of said slot thereby defining an elongated mesiodistally extending rectilinear archwire engaging face for engaging a substantial length of the archwire to control mesiodistal inclination between the bracket and archwire.

2. The lock pin defined in claim 1, wherein said tail extends lingual to the archwire.

3. The lock pin defined in claim 2, wherein said bracket coacting means includes a portion along the tail having a mesiodistal width such as to snugly fit between the attaching flanges in the area of the slot.

4. The lock pin defined in claim 3, wherein said means further includes an indentation in the head for telescopically receiving the body at the archwire slot.

5. The lock pin defined in claim 1, wherein said means includes an indentation in the head for telescopically receiving the body at the archwire slot.

6. The lock pin defined in claim 1, wherein the mesiodistal width of said head is substantially equal to the mesiodistal width of the entire bracket such that the archwire engaging face extends beyond the opposite sides of the body.

7. The lock pin defined in claim 1, wherein the mesiodistal width of said head is substantially equal to the mesiodistal width of the body and one of the attaching flanges such that the archwire engaging face extends substantially across the slot and along one of the attaching flanges.

8. The lock pin defined in claim 1, wherein the face of the head extends perpendicular to the long axis of the tail.

9. The lock pin defined in claim 1, wherein the included angle between the face of the head and the long axis of the tail on the mesial side is less than ninety degrees.

10. The lock pin defined in claim 1, wherein the included angle between the face of the head and the long axis of the tail on the mesial side is more than ninety degrees.

11. The lock pin defined in claim 1, which further includes an extension on the head extending beyond the bracket and serving to connect a ligature between the head and archwire.

12. The lock pin defined in claim 1, wherein said tail extends buccal to the archwire.

13. The lock pin defined in claim 12, wherein said bracket coacting means includes at least one ear extending from the head along at least one side of said tail to engage the bracket body and enhance stability between the pin and bracket.

14. The lock pin defined in claim 12, wherein said bracket coacting means includes a pair of ears extending from the head, one along each side of the tail to engage along each side of the bracket body, said ears extending a sufficient distance beyond the archwire engaging face and the bracket slot so that at least one ear can be bent over the archwire to provide additional control between the pin and archwire.

15. The lock pin defined in claim 14, wherein the lingual surface of at least one ear is scored to permit easy bending of said ear over an archwire.

16. The lock pin defined in claim 12, which further includes an offset lug extending from the head into the area between the attaching flanges and lingual of said archwire.

17. In combination with a bracket having a body with an occlusogingivally extending opening, a mesiodistally extending archwire slot, and attaching flanges at the lingual side of the body, a lock pin for locking one or more archwires in the bottom of the slot comprising a tail extending into said opening lingual of said archwire and having a mesiodistal width along a part thereof to snugly fit between said attaching flanges in the area of said slot to prevent relative rotational movement between the bracket and the pin, and a head integral with and in overlapping abutting relation to the tail and received in said slot in overlying relation to said archwire and having a mesiodistal width at least equal to about one-half the mesiodistal width of the bracket to define an elongated archwire engaging face for engaging a substantial length of the archwire to control mesiodistal inclination between the bracket and archwire.

18. The lock pin defined in claim 17, wherein the mesiodistal width of the head is substantially greater than that of said tail part such that it extends through said slot and beyond both mesial and distal sides of said body to provide an elongated archwire engaging face for controlling mesiodistal inclination.

19. In combination with a bracket having a body with an occlusogingivally extending opening, a mesiodistally extending archwire slot, and attaching flanges at the lingual side of the body, a lock pin for locking one or more archwires in the bottom of the slot comprising a tail extending into said opening labial of said archwire, a head integral with the tail and doubled back over the tail, said head having an archwire engaging portion received in said slot in overlying relationship to said archwire and of a mesiodistal width substantially equal to the mesiodistal width of the bracket thereby defining an elongated archwire engaging face extending both mesially and distally of the bracket body and engaging a substantial length of the archwire to control mesiodistal inclination between the bracket and archwire, and said head further including a pair of ears, one each extending along each side of said tail and along the respective outer surface of said body and to coact therewith to provide stability between the pin and bracket and prevent relative rotational movement between the pin and bracket about the labiolingual axis of the bracket.

20. The lock pin defined in claim 19, wherein said ears extend labially over the archwire to give rotational control over the tooth on which the bracket is mounted.

21. The lock pin defined in claim 19, wherein said ears terminate beyond said archwire engaging face so that one or both can be bent over the archwire to provide further control between the bracket and archwire.

22. The lock pin defined in claim 19, wherein at least one of the ears terminates beyond said archwire engaging face so that it may be bent over the archwire to provide further control between the bracket and the archwire.

23. The lock pin defined in claim 19, which further includes a lug extending lingually from the archwire engaging portion to fit between the bracket attaching flanges and provide better control between the bracket and archwire and hold the archwire more positively in said slot.

24. In combination with a bracket having a body with an occlusogingivally extending opening, a mesiodistally extending archwire slot, and attaching means at the lingual side of the body, a lock pin for locking one or more archwires in the bottom of the slot comprising a tail extending into said opening labial of said archwire, a head integral with the tail and having an archwire engaging portion received in said slot in overlying relationship to said archwire and of a mesiodistal width substantially equal to the mesiodistal width of the bracket thereby defining an elongated archwire engaging face extending both mesially and distally of the bracket body and engaging a substantial length of the archwire to control mesiodistal inclination between the bracket and archwire, and said head further including at least one ear extending along one side of said tail to coact with the body and prevent relative rotational movement between the pin and bracket along a labiolingual axis of the bracket and labially over the archwire to give rotational control over the tooth on which the bracket is mounted.

25. The lock pin defined in claim 24, which further includes a lug extending lingually from the archwire engaging portion to fit between the bracket attaching flanges and provide better control between the bracket and archwire and hold the archwire more positively in said slot.

* * * * *

UNITED STATES PATENT AND TRADEMARK OFFICE
CERTIFICATE OF CORRECTION

PATENT NO. : 4,350,487
DATED : September 21, 1982
INVENTOR(S) : Peter C. Kesling and Dennis B. Henderlong It is certified that error appears in the above—identified patent and that said Letters Patent is hereby corrected as shown below:

Col. 8, line 52, delete "a" and insert therefor
--an elastomeric--

Signed and Sealed this

Eighth Day of February 1983

[SEAL]

Attest:

GERALD J. MOSSINGHOFF

Attesting Officer

Commissioner of Patents and Trademarks